United States Patent [19]

Deasy

[11] Patent Number: 5,418,715
[45] Date of Patent: May 23, 1995

[54] METHOD OF ELECTRON BEAM RADIOTHERAPY

[75] Inventor: Joseph O. Deasy, Middleton, Wis.

[73] Assignee: Wisconsin Alumni Research Foundation, Madison, Wis.

[21] Appl. No.: 213,405

[22] Filed: Mar. 15, 1994

[51] Int. Cl.⁶ ......................... G06F 15/00; A61N 5/10
[52] U.S. Cl. ................................ 364/413.26; 378/65
[58] Field of Search .................... 364/413.26, 413.13; 378/65, 97, 69; 128/653.1; 250/505.1

[56] References Cited

U.S. PATENT DOCUMENTS

| | | | |
|---|---|---|---|
| 3,794,840 | 2/1974 | Scott | 250/363 |
| 3,987,281 | 10/1976 | Hodes | 364/413.26 |
| 4,729,099 | 3/1988 | Iverson et al. | 364/413.26 |
| 5,027,818 | 7/1991 | Bova et al. | 364/413.22 |
| 5,291,404 | 3/1994 | Kurokawa et al. | 364/413.26 |

Primary Examiner—Robert A. Weinhardt
Assistant Examiner—Xuong My Chung-Trans
Attorney, Agent, or Firm—Quarles & Brady

[57] ABSTRACT

A computationally efficient and accurate procedure for calculating electron beam dose within a volume of a patient incorporating knowledge about the variations in density of the patient as obtained from a CT machine or the like employs an iterative process of dividing the patient into a set of layers of elements where each layer is computed from the previous layer by algebraic approximations of the Fermi partial differential equation. Energy loss of the particles is accommodated through the addition of a simple functional relationship between depth and energy or by separately binning energy at each layer as determined by local energy loss.

9 Claims, 3 Drawing Sheets

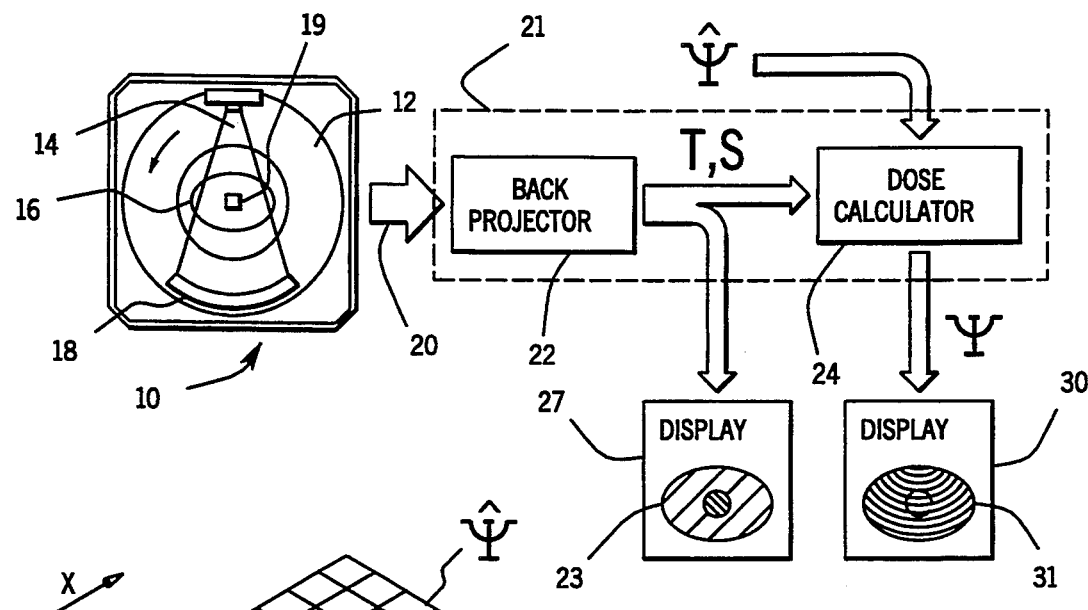
FIG. 1
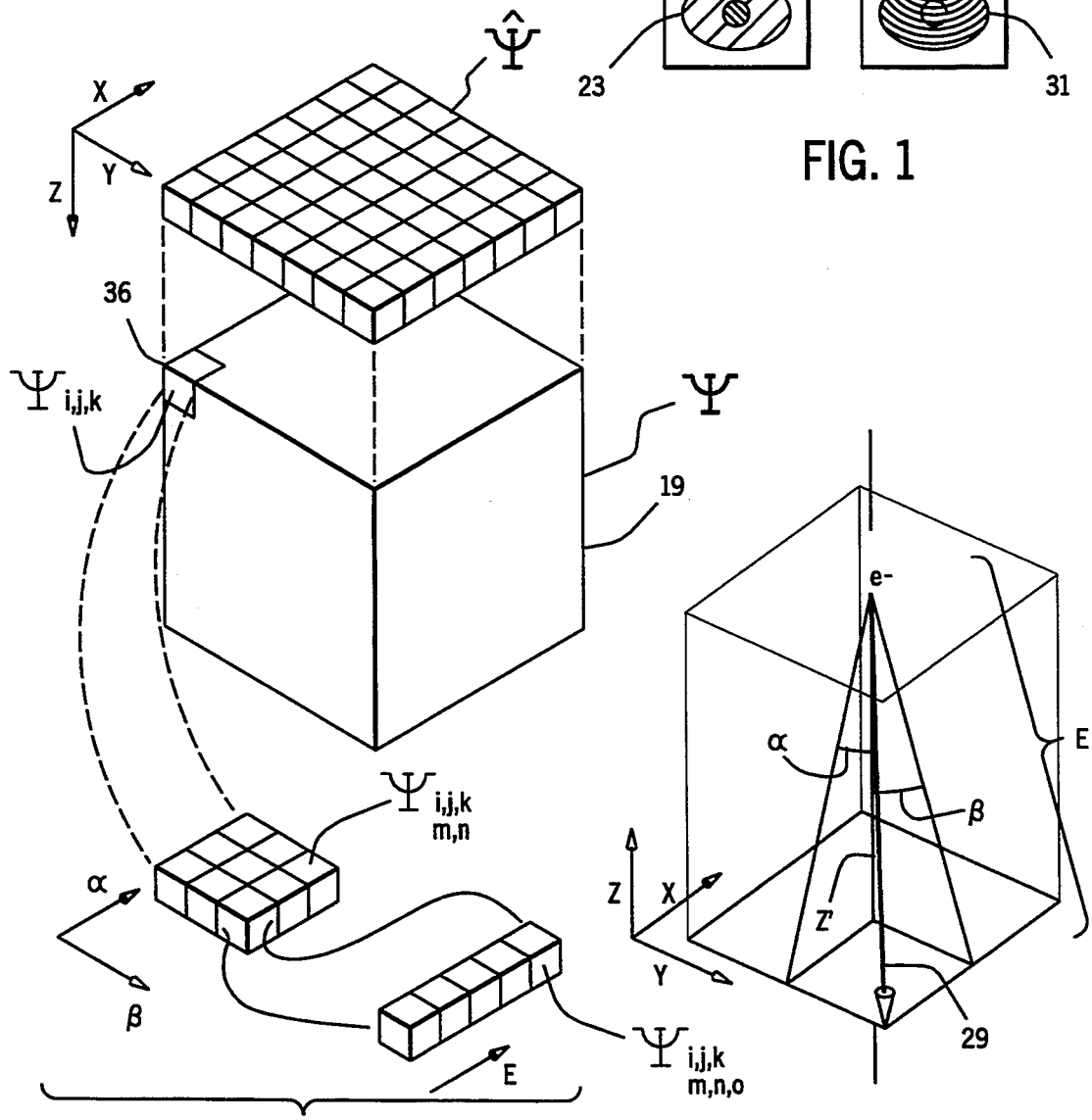
FIG. 2
FIG. 3

METHOD OF ELECTRON BEAM RADIOTHERAPY

BACKGROUND OF THE INVENTION

1. Field of the Invention

This invention relates generally to radiation therapy equipment for the treatment of tumors, or the like, and specifically to a computerized method of evaluating dose levels in electron beam radiotherapy treatment.

2. Background Art

Medical equipment for radiation therapy treats tumorous tissue with high energy radiation. The amount of radiation and its placement must be accurately controlled to ensure both that the tumor receives sufficient radiation to be destroyed, and that damage to the surrounding and adjacent non-tumorous tissue is minimized.

Internal source radiation therapy places capsules of radioactive material inside the patient in proximity to the tumorous tissue. Dose and placement are accurately controlled by the physical positioning of the isotope. However, internal source radiation therapy has the disadvantage of any surgically invasive procedure, including discomfort to the patient and risk of infection.

External source radiation therapy uses a radiation source that is external. The source of the high energy radiation may be x-rays, or electrons from linear accelerators in the range of 2 to 25 MeV, or gamma rays from highly focused $Co^{60}$ sources having an energy of 1.25 MeV. The external source is collimated to direct a beam into the patient to the tumor site.

Although the size and strength of the radiation beam from the external source may be accurately controlled outside of the patient, the dose received by a given volume within the patient may vary because of scattering and absorption of the radiation by the intervening tissue. For this reason, a determination of the proper dose and placement of the dose requires an estimation of the effects of treated tissue and the tissue surrounding the treated area in scattering or attenuating the radiation beam.

With electron beam radiotherapy equipment, the scattering of the electrons as they interact with medium is described by Fermi's partial differential equation:

$$\Psi_z = -\alpha\Psi_x + (T/4)\Psi_{\alpha\alpha} - \beta\Psi_y + (T/4)\Psi_{\beta\beta} \quad (1)$$

where $\Psi$ is a function of the Cartesian coordinates x, y and z describing the density of electrons (flux) at points within the volume of the medium and of angles $\alpha$ and $\beta$ which describe the trajectory of the electrons with respect to the z axis, and where $\Psi_z$, $\Psi_x$, and $\Psi_y$ are the partial derivatives of $\Psi$ with respect to x, y and z; $\Psi_{\alpha\alpha}$ and $\Psi_{\alpha\alpha}$ are the second partial derivative of $\Psi$ with respect to angles $\alpha$ and $\beta$ respectively, and T is the scattering power of the medium through which the radiation travels. In general, T will vary throughout the volume and will therefore be a function of x, y and z.

Analytic solutions to Fermi's partial differential equation, that is, algebraic functions $\Psi(x,y,z,\alpha,\beta)$ that meet the requirements of equation (1), are difficult to determine in all but a few simple cases. Those simple cases include that where the patient is homogeneous or where the values of T varies only as a function of z. Neither of these cases accurately describe many volumes within a patient where radiotherapy may be required.

Failure to accurately account for variations in the value of T in the x and y directions may lead to "hot" or "cold" spots where substantially more or less radiation is delivered than desired. This is especially true in the neighborhood of substantial x and y variations in density such as may occur if the tumor to be treated is near a cavity or bone.

For this reason, a "Monte Carlo" method is presently preferred for the calculation of radiation dose for electron beam radiotherapy. In this technique, the paths of several million particles are traced through a model of the patient which accurately reflects the three dimensional variations in the value of T within the volume being studied. At regular points along the path of each electron as modeled, a probability of scattering is calculated based on the value of T at that point. For large numbers of electrons (above $10^6$) an accurate representation of the dose is obtained.

Unfortunately, the Monte Carlo method is extremely time consuming and may take upwards of several hours for the computation of a single dose on current electronic computers.

The need exists for a method of dose modeling accurately accounting for variations in T and that has greater computational efficiency than the Monte Carlo technique.

SUMMARY OF THE INVENTION

The present invention provides a method of discretizing Fermi's partial differential equation so as to take into account local changes in density of the patient at different points in the treated volume. Flux is iteratively calculated at a series of thin but successively deeper layers across small volume elements which have essentially constant densities and where algebraic approximations may be substituted for the partial derivatives of Fermi's partial differential equation.

Specifically, the method evaluates dosage patterns in electron beam radiotherapy where an electron beam is directed at a volume of interest in a patient having Cartesian dimensions x, y and z. The resulting dosage pattern within the patient can be deduced from an electron flux matrix $\Psi$ of incident electron flux definable at elements spatially dispersed within the volume of interest and identified to particular angular trajectories $\alpha$ and $\beta$ with respect to an axis in the z dimension. The method employs an electronic computer into which a matrix T has been entered describing scattering power of the tissue of the patient at the elements within the volume of interest, and into which an incident flux field $\Psi$ has been entered having values corresponding to the electron flux of electrons entering the region of interest. The electronic computer is programmed to generate from an initial matrix layer (originally equal to the incident flux field $\Psi$) and through an algebraic approximation of Fermi's partial differential equation, a next matrix layer offset by a predetermined amount in z. This next matrix layer is then stored in computer memory. The initial matrix layer is then set equal to the next matrix layer and these steps are repeated until a next matrix layer has been determined for the entire volume of interest.

Thus, it is one object of the invention to provide a method of dose calculation that is more computationally efficient than the Monte Carlo method presently employed but that employs a complete set of information about variations in T.

The algebraic approximation of Fermi's partial differential equation may be used to derive both flux and energy values for each next matrix layer and wherein the flux values may be stored separately by energy. Alternatively energy may be derived as a function of z depth.

Thus, it is another object of the invention to provide a computationally efficient method of treating the energy loss mechanism of particle beam radiation therapy.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

BRIEF DESCRIPTION OF THE DRAWINGS

FIG. 1 is a block diagram showing the generation of a scattering power matrix T and stopping power matrix S for a slice through a patient by means of a CT machine and the computer calculation of an electron flux matrix $\Psi$ in that slice of the patient based on an incident flux field $\Psi$ representing the known strength of the incident electron beam;

FIG. 2 is a diagrammatic representation of the incident flux field $\Psi$ and the electron flux matrix $\Psi$ showing elements of that matrix arrayed in space and as further subdivided according to electron angles $\alpha$ and $\beta$ and electron energies E;

FIG. 3 is a diagrammatic representation of a single electron within one element of the electron flux matrix $\Psi$ of FIG. 2, showing the trajectory of the electron defined by angles $\alpha$ and $\beta$ within a region defined by Cartesian coordinates x and y and z and of an energy E;

DETAILED DESCRIPTION OF THE PREFERRED EMBODIMENT

Hardware

Figure 4:
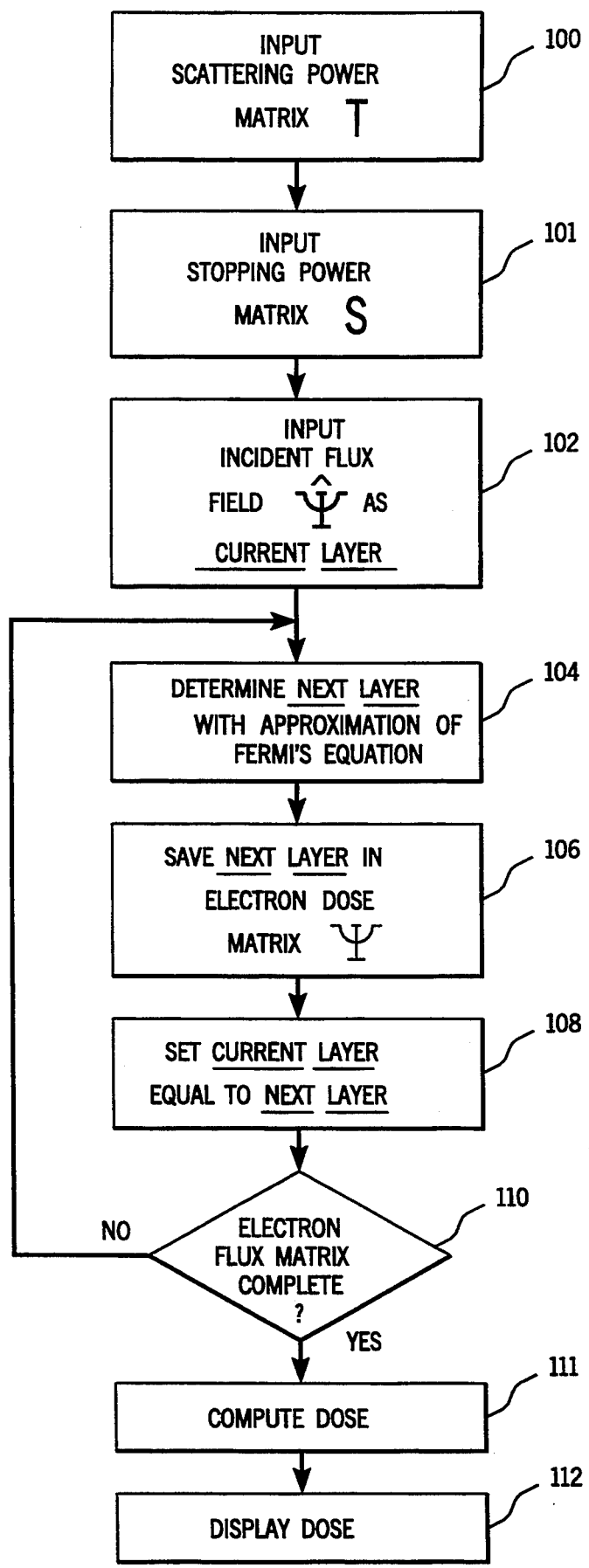
FIG. 4 is a flow chart of the steps of the computer program performed by the computer of FIG. 1 showing the iterative calculation of the electron does matrix $\Psi$ for the scattering power matrix $\Psi$ and the incident flux field $\Psi$.

Referring to FIG. 1, a computed tomography ("CT") machine 10 employs a rotating gantry 12 for projecting a fan beam of radiation 14 through a patient 16 at various angles about the patient 16. A detector array 18 acquires projection data 20 at each of these angles of the gantry 12. The projection data is backprojected 22 on an electronic computer 21 to form a tomographic image 23 providing flux information throughout a volume of interest 19 of the patient 16 as may be stored in computer memory (not shown) and displayed on display device 27. The volume of interest 19 is selected to cover a tumor to be treated in radiation therapy. Computed tomography systems and computer systems for use with such systems are well known in the art.

Data Structures

The Scattering Power Matrix T

The density information of the tomographic image 23 may be used to construct a scattering power matrix T indicating the scattering power of each volume element ("voxel") of the volume of interest 19, and a stopping power matrix S indicating the stopping power of each voxel of the volume of interest. As the names would indicate, "scattering" is the measure of a material's ability to change the trajectory of the electron without stopping it, whereas "stopping" is the measure of the ability of a material to stop the electrons by absorbing their energy. There are a number of techniques for estimating "scattering" and "stopping" from CT data and assumptions about the composition of the patient, that are well known in the art.

The storage of the matrices T and S in a computer 21 is accomplished by equating an address in the computer's memory, used to hold the contents of each element of the matrices, with the various matrix dimensions so that the address uniquely identifies the location of the particular element within the matrices' multiple dimensions. The contents of each element of the matrix is simply a number. In the case of the scattering power matrix T that number is the scattering power associated with the given voxel of the patient 16, and in the case of stopping power matrix S, that number is the stopping power associated with the given voxel of the patient 16. Within this description, such arrays are designated by bold face symbols, e.g. T, S.

Thus, the scattering power matrices T and S provide scattering information throughout the volume of interest 19 at matrix elements, generally identified to the Cartesian coordinates of their associated voxels within the volume of interest 19. These matrices will generally be of three dimensions corresponding to the dimensions of the volume of interest 19.

The Incident flux field $\Psi$

Referring still to FIG. 1, the scattering power matrix T is combined with another matrix, an incident flux field $\Psi$, in a dose calculator 24 (to be described). The incident flux field $\Psi$, represents the flux of electrons entering the volume of interest 19 along the z direction at each point along a surface in x and y. The incident flux field $\Psi$ is normally inferred from water phantom measurement of dose and will be dependent on the particular radiotherapy machine to be employed and the setting and calibration of that machine.

Referring to FIGS. 2 and 3, the incident flux field $\Psi$ requires for its description and for its storage in the computer 21 at least a two dimensional array of elements in x and y, each element holding a number indicating the flux of electrons from the radiotherapy machine incident to the volume of interest 19. Thus each electron $e^-$ may be identified to a region within the x–y plane by its element in a two dimensional array. More generally, however, each electron $e^-$, of the incident flux field $\Psi$ may also be characterized by the angle of its trajectory 29 and by its energy. The angle of its trajectory 29 may be described by angles $\alpha$ and $\beta$ where 60 is the angle between the z-axis and a projection of the electrons trajectory 29 on the x-z plane and $\beta$ is the angle between the z-axis and the projection of the electron's trajectory 29 on the z–y plane.

Typically, however, the energy and trajectory of the electrons in the incident flux field $\Psi$ will be uniform over the x-y plane. The energy is that set by the radiotherapist and the trajectory is nearly parallel to the z axis.

The Electron Flux Matrix $\Psi$

As the electrons of the incident flux field $\Psi$ pass into the volume of interest 19, traveling generally along the z direction, they impart a radiation dose to each voxel of the volume of interest. The flux at each point is calculated from the scattering power matrix T and the incident flux field $\Psi$ in the dose calculator 24 to produce an electron flux matrix $\Psi$. The electron flux matrix $\Psi$ is generally three-dimensional to match the volume of interest 19, however, "slices" of the electron flux matrix $\Psi$ may be displayed on a display 30 as an image 31 of isodose lines superimposed on a slice image 31 formed from the backprojected CT data. The elements of the three-dimensional electron flux matrix $\Psi$ at a given z value will be termed a "layer" with the electrons passing first through the "upper" layers of the electron flux matrix $\Psi$.

The present invention employs the electron flux matrix $\Psi$ not only to describe the flux throughout the volume of interest 19 but also in determining that flux iteratively, on a layer by layer basis. That is, upper layers are used to deduce the electron flux for lower layers.

In order to provide the necessary information for this iterative process, the electron flux matrix $\Psi$, provides not only the flux at spatial locations, but also provides information necessary to track the progression of the electrons through the patient 16. This tracking requires that the electron flux matrix $\Psi$ record the trajectories of the electrons in each voxel, as measured by $\alpha$ and $\beta$, and in one embodiment, the energies E of the electrons. The need to characterize the electrons as to their energies E arises because electrons having insufficient energy may simply stop at a preceding layer.

This additional information of $\alpha$, $\beta$, and E is represented in FIG. 3 as additional bins within each elements 36 of the region of interest 19. The visual representation of FIG. 3 of the subpartitioning of each element into $\alpha$ and $\beta$ and E is intended to provide an intuitive framework for this multidimensional array. Nevertheless, it will be recognized that the electron flux matrix $\Psi$ is simply a six dimensional array with no particular hierarchy among the dimensions.

As a practical matter, just as the Cartesian space of the region of interest 19 is quantized into discrete elements, the angles $\alpha$ and $\beta$ are divided into discrete ranges in the preferred embodiment being 2° and the energy E divided in to bands of 0.23 Mev, each band or range being a separate bin. For notational clarity, each element of the electron flux matrix $\Psi$ is designated by a set of index numbers corresponding to each of the dimensions of the electron flux matrix $\Psi$. Variables i, j, and k are used to represent these index numbers for the x, y and z dimensions, respectively—greater values of z are lower layers of the electron flux matrix $\Psi$. Variables n and m refer to the index numbers associated with the dimensions of $\alpha$ and $\beta$. The variable o designates the dimension of E, when used.

The Dose Calculator

The dose calculator 24, like the backprojector 22, may be realized in software in the computer 21. Referring now to FIG. 4, at the first step of the program implementing the dose calculator, the scattering power matrix T is input as indicated by process block 100. At succeeding process block 101, the stopping power matrix S is also entered to be used in the calculation of dose to be described below and the incident flux field $\Psi$ is input to the computer 21 as indicated by process block 102. The incident flux field $\Psi$ is saved in a current layer variable, the variable is an array equal in size to that of the incident flux field $\Psi$ and is used in subsequent calculations.

At process block 104, values for a next layer variable equal in size to the current layer is calculated from the current layer by using an algebraic approximation to Fermi's partial differential equation (1) given above. Equation (1) provides an accurate mathematical description of the scattering of a large number of charged particles passing through a medium in the form of a relatively simple relationship between the partial derivatives of the particle densities along the coordinates x, y, z, $\alpha$ and $\beta$. Nevertheless, as has been described above, analytic solutions, that is, sets of values fitting the requirements of equation (1) have only been determined for some relatively simple cases with often unrealistic simplifying assumptions about the variations of T throughout the scattering medium.

By discretizing the electrons and their trajectories into the current layer and next layer variables, it has been determined that Fermi's partial differential equation may be accurately approximated algebraically for the small regions defined by the separation between elements of the current and next layer variables. One such algebraic approximation uses the following relations:

$$\Psi_z \approx (\Psi_{m,n}{}^{i,j,k+1} - \Psi_{m,n}{}^{i,j,k})/\Delta z \qquad (3)$$

$$\Psi_x \approx (\Psi_{m,n}{}^{i-1,j,k} - \Psi_{m,n}{}^{i+1,j,k})/2\Delta x \qquad (4)$$

$$\Psi_y \approx (\Psi_{m,n}{}^{i,j-1,k} - \Psi_{m,n}{}^{i,j+1,k})/2\Delta y \qquad (5)$$

$$\Psi_{\alpha\alpha} \approx (\Psi_{m-1,n}{}^{i,j,k} - 2\Psi_{m,n}{}^{i,j,k} + \Psi_{m+1,n}{}^{i,j,k})/(\Delta\alpha)^2 \qquad (6)$$

$$\Psi_{\beta\beta} \approx (\Psi_{m,n-1}{}^{i,j,k} - 2\Psi_{m,n}{}^{i,j,k} + \Psi_{m,n+1}{}^{i,j,k})/(\Delta\beta)^2 \qquad (7)$$

where $\Delta x$, $\Delta y$, $\Delta z$, $\Delta\alpha$, and $\Delta\beta$ are the spatial and angular separations between elements and bins of the electron flux matrix $\Psi$ (hence $\Delta z$ is also the separation between layers). The subscripts and superscripts following $\Psi$ are simply the index variables referred to above. These approximations will be recognized as the definition of a partial derivative when the denominator values approach zero.

Thus in process block 104, the approximations of equations (3)–(7) are substituted into equation (1) and the resulting combination solved for $\Psi_{m,n}{}^{i,j,k+1}$, where i,j, k+1, m, and n, are the coordinates of the element and bin of the next layer variable being determined at any given instant.

Thus, each element of the next layer may be computed from neighboring elements of the current layer above it. The first time this calculation is performed, as mentioned, the current layer is the incident flux field $\Psi$.

For a simplified case of a two dimensional volume of interest 19 where the change in scattering power T in the y direction is constant. Equation (1) will simplify to:

$$\Psi_z = -\alpha\Psi_x + (T/4)\Psi_{\alpha\alpha} \qquad (8)$$

and the use of these approximations will result in the following formula for computing the electron flux at a given element 36.

$$\Psi_m^{i,k+1} = \frac{\Psi_m^{i-1,k} \Delta z \Delta \alpha \alpha}{2\Delta x} - \frac{\Psi_m^{i+1,k} \Delta z \Delta \alpha \alpha}{2\Delta x} + \quad (9)$$

$$\frac{\Psi_{m-1}^{i,k} \Delta z T}{4\Delta \alpha^2} + \frac{\Psi_{m+1}^{i,k} \Delta z T}{4\Delta \alpha^2} + \Psi_m^{i,k}\left(1 - \frac{\Delta z T}{2\Delta \alpha^2}\right)$$

It will be noted in this equation (9) only algebraic operators are required (addition, subtraction, division and multiplication) and that no integral or derivative operators are required. Further, significant portions of the equation are constants depending on the fixed and predetermined $\Delta$ values that may be precomputed and thus require no real-time computational effort by the electronic computer 21. It will be noted that with sufficiently small increments between layers, that the value of T will be essentially constant thus further simplifying the calculation of each succeeding layer. The expansion of equation (9) to the three dimensional case is a routine exercise of algebraic manipulation.

Other approximations of the partial derivatives of the Fermi equation are possible. For example, a combination of the Lax-Wendroff method for solving the inhomogeneous one-way wave equations (which has the form $f_z + Af_z = h$) may be used, with h replaced by equation (6) to represent equation (1). Here $\Psi_{m,n}^{i,j,k+1}$ is given as follows:

$$\Psi_m^{i,k+1} = \psi_m^{i+1,k}\left(\frac{-0.5\Delta z \Delta \alpha \alpha}{\Delta x} + \frac{0.5\Delta z^2 \Delta \alpha^2 \alpha^2}{\Delta x^2}\right) + \quad (10)$$

$$\psi_m^{i-1,k}\left(\frac{0.5\Delta z \Delta \alpha \alpha}{\Delta x} + \frac{0.5\Delta z^2 \Delta \alpha^2 \alpha^2}{\Delta x^2}\right) + \frac{\Delta z^2 \Psi_{m-2}^{i,k} \alpha T}{16\Delta x \Delta \alpha} -$$

$$\frac{\Delta z^2 \Psi_{m+2}^{i,k} \alpha T}{16\Delta x \Delta \alpha} + \Psi_m^{i,k}\left(1 - \frac{\Delta z^2 \Delta \alpha^2 \alpha^2}{\Delta x^2} - \frac{\Delta z T}{2\Delta \alpha^2}\right) +$$

$$\Psi_{m-1}^{i,k}\left(\frac{\Delta z T}{4\Delta \alpha^2} - \frac{\Delta z^2 \alpha T}{8\Delta x \Delta \alpha}\right) + \Psi_{m+1}^{i,k}\left(\frac{\Delta z T}{4\Delta \alpha^2} - \frac{\Delta z^2 \alpha T}{8\Delta x \Delta \alpha}\right)$$

Referring again to FIG. 4, at process block 106, the next layer variable, at the given index value of k+1 is next stored in the appropriate layer of the evolving electron flux matrix $\Psi$ and used to replace the contents of the current layer variable at process block 108.

At decision block 110, a check is made to see if the entire volume of interest 19 has had its flux computed through successive layers and, if not, the program branches back to process block 104 and a further next layer is computed based on the new current layer. Thus, each succeeding layer of electron flux matrix $\Psi$ is computed from the preceding layer in incremental steps of sufficiently fine resolution that the algebraic approximations of equations (3)–(7) hold true.

Importantly, the calculation of each element in a given next layer may refer only to a few neighboring elements of the previous current layer and thus there is no requirement that over the entire x–y plane that the value of T be constant. Thus, the full value of the information obtained in a CT scan of the volume of interest 19 may be exploited.

If the full volume of interest has been computed, the electron flux matrix $\Psi$ will be used to compute the dose at each voxel as indicated by process block 111. The dose is calculated by summing the flux through a voxel over all angles $\alpha$ and $\beta$ and all energies E (if energies are tracked) as follows $$D(x,y,z) = \int_0^{\pi/2} d\alpha \int_0^{\pi/2} d\beta \Psi(\alpha,\beta,x,y,z) \frac{S(x,y,z)}{\cos\theta}. \quad (11)$$

$$(\theta^2 = \alpha^2 + \beta^2)$$

The dose may be outputted or displayed for review by a physician per process block 112. The display may include the highlighting of dose levels that exceed predetermined values outside of the tumor or that drop below predetermined values inside the tumor. This process of determining if the dose is adequate may be automated by inputting the spatial limits of the tumor to the computer by means of a tracing or other methods known in the art. Thus, the dose may be evaluated and the radiation input as the incident flux field $\Psi$ may be varied within certain limits to improve that dose. As more sophisticated electron beam radiation treatment machines become available, with the ability to vary the incident flux field $\Psi$ within the x-y plane, the method of the present invention may be employed to help optimize more complex definitions of incident flux field $\Psi$ in an iterative fashion.

EXAMPLE 1

Figure 5:
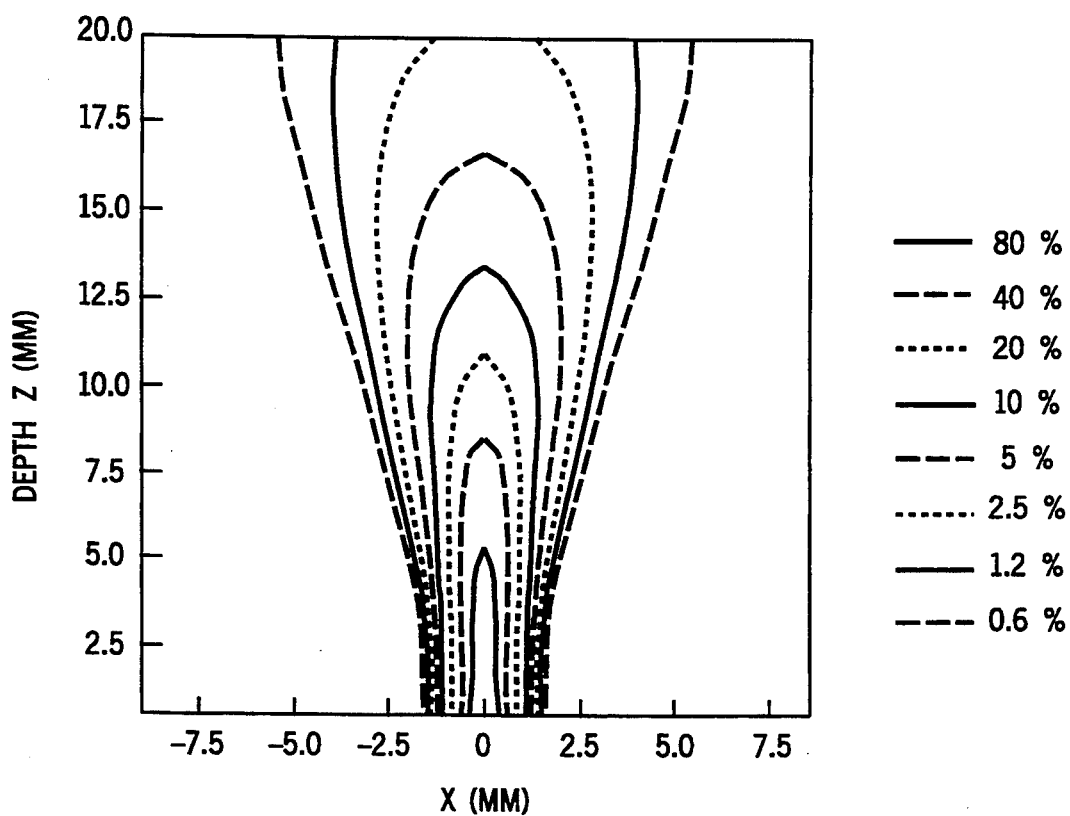
FIG. 5 is a graph of isodose lines within the electron flux matrix $\Psi$ for an incident flux field $\Psi$ consisting of a ten MeV pencil beam passing through water as simulated by the method of FIG. 4.

Penetration of 10-MeV electrons into water was simulated using the finite difference approximation and the Lax-Wendroff approximation as described above. The spacing of the elements of the region of interest was as follows: $\Delta z + 0.5$ mm, $\Delta x = 0.5$ mm, $\Delta \alpha = 2°$, $\Delta \beta = 2°$. The mass scattering power used was T=0.07 rad$^2$/(g/cm$^2$) appropriate for 10-MeV electrons in water. Energy loss was not taken into account in this initial test. FIG. 5 shows the dose calculation using the modified Lax-Wendroff method. The isodose lines are labeled as a percentage of the maximum dose. The incident beam was modeled as mono-directional and having a Gaussian spatial spread with a standard deviation of 0.5 mm. It was found that using a pencil beam reduced to a single X grid point resulted in a "jagged" dose distribution. However, the jaggedness of the dose irregularities were smoothed out by including contributions from pencil beams incident at neighboring points.

Figure 6:
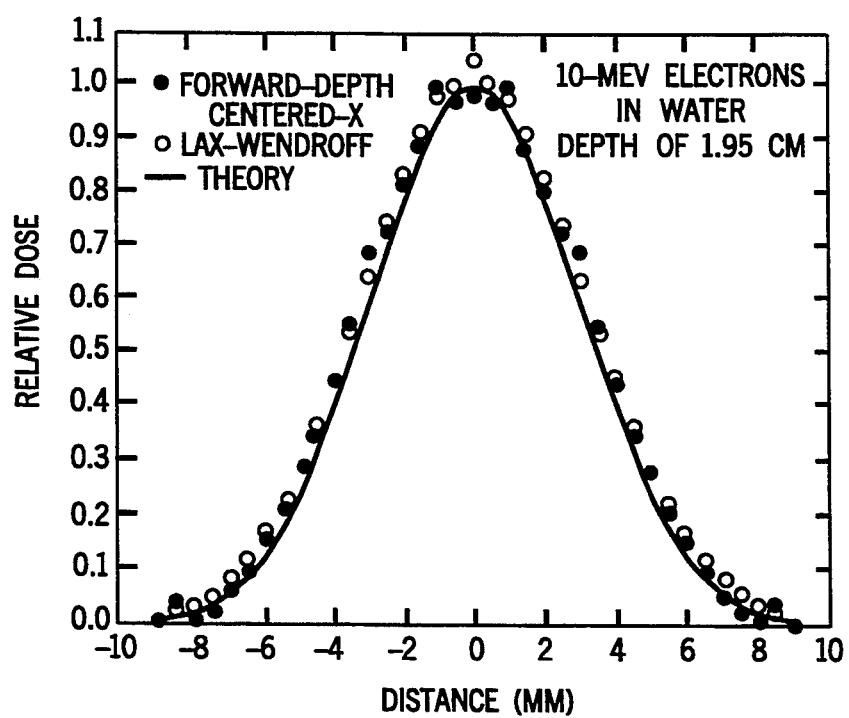
FIG. 6 is a graph comparing the electron flux matrix $\Psi$ of FIG. 5 at a depth of 1.95 cm according to the methods of FIG. 4 and according to analytic theory.

FIG. 6 compares the lateral dose profiles for the two finite difference schemes and the known theoretical solution which includes the effects of incident pencil beam width at a depth of 1.95 cm. The agreement is good. The difference between the spatial widths of the finite difference results and the theoretical curve is consistent with the half-width of the incident angular bin 2°. As expected, the higher order Lax-Wendroff scheme gives a smoother distribution than the forward depth centered X method.

Energy Considerations

The modeling of scattering alone, as described above, offers an improved determination of dose over previous methods employing analytic solutions to Fermi's partial differential equation. Nevertheless, in a second embodiment, not only is the scattering of electrons as they pass through the medium taken into account but also the loss of energy of the electrons so that the mechanism of electrons stopping and no longer proceeding to subsequent layers may be accommodated.

Thus, taking into account changes in electron energy may be done by including the partitions of energy E in each of the elements of the electron flux matrix $\Psi$ of the region of interest 19 and using a expanded form of Fermi's equation as follows:

$$\Psi_z = -\alpha\Psi_x + (T/4)\Psi_{\alpha\alpha} - \beta\Psi_y + (T/4)\Psi_{\beta\beta} + \Psi_E S \quad (12)$$

where S is the stopping power described above and $\Psi_E$ is the partial derivative of $\Psi$ with respect to energy. This equation may be discretized in a manner analogous to that described above with respect to equations (3)-(7) using the following equations (13)-(18)

$$\Psi_z \approx (\Psi_{m,n,o}^{i,j,k+1} - \Psi_{m,n,o}^{i,j,k})/\Delta z \quad (13)$$

$$\Psi_x \approx (\Psi_{m,n,o}^{i-1,j,k} - \Psi_{m,n,o}^{i+1,j,k})/2\Delta x \quad (14)$$

$$\Psi_y \approx (\Psi_{m,n,o}^{i,j-1,k} - \Psi_{m,n,o}^{i,j+1,k})/2\Delta y \quad (15)$$

$$\Psi_{\alpha\alpha} \approx (\Psi_{m-1,n,o}^{i,j,k} - 2\Psi_{m,n,o}^{i,j,k} + \Psi_{m+1,n,o}^{i,j,k})/(\Delta\alpha)^2 \quad (16)$$

$$\Psi_{\beta\beta} \approx (\Psi_{m,n-1,o}^{i,j,k} - 2\Psi_{m,n,o}^{i,j,k} + \Psi_{m,n+1,o}^{i,j,k})/(\Delta\beta)^2 \quad (17)$$

$$\Psi_E \approx (\Psi_{m,n,o-1}^{i,j,k} - \Psi_{m,n,o}^{i,j,k})/\Delta o \quad (18)$$

Thus, the history of each electron is preserved along with the energy of each electron. The drawback to this approach is that it requires a number of additional bins in the electron flux matrix $\Psi$ thus significantly increasing the time of the matrix calculation.

An alternative method makes the energy of each electron simply a function of its depth within the region of interest 19. For each vertical column through the patient (having constant x and y) an analytic solution to Fermi's equation (12) may be determined by assuming the scattering power T of the patient is homogenous in the x and y directions and assuming an incident pencil beam of electrons. The z dependency of T is deduced from the CT data as described above only for the values of x and y of the column. Such analytic solutions are known in the art.

The energy of the electrons in each voxel of that vertical column is then simply set equal to the energy indicated by this analytic solution with a pencil beam having initial flux and energy given by the incident flux field $\Psi$ for the x and y values describing the column under consideration.

In summary, the present invention, by discretizing the problem of dose calculation and in treating the calculation on a layer by layer basis, significantly increases the speed and accuracy at which doses may be calculated and provides for a means of introducing information with regard to the variation in scattering power of a patient's tissue such as may be developed by presently available computed tomography equipment.

The above description has been that of a preferred embodiment of the present invention. It will occur to those that practice the art that many modifications may be made without departing from the spirit and scope of the invention. In order to apprise the public of the various embodiments that may fall within the scope of the invention, the following claims are made.

I claim:

1. A method of irradiating a patient with electron beams directed at a volume of interest in the patient having Cartesian dimensions x, y and z, with a dosage pattern described by the matrix D and electron flux within the patient defined by the matrix $\Psi$ at elements spatially dispersed within layers of constant z in the volume of interest and further identified to particular angular trajectories $\alpha$ and $\beta$ with respect to an axis in the z dimension, the method comprising the steps of:
   (a) providing to an electronic computer:
      (i) a matrix T describing the scattering power of the patient at the elements within the volume of interest;
      (ii) an incident field $\Psi$ having values corresponding to the electron flux of the electrons entering the region of interest;
   (b) instructing the electronic computer to:
      (i) set an initial matrix layer equal to the incident field $\Psi$;
      (ii) generate from the initial matrix layer $\Psi$ through an algebraic approximation of Fermi's partial differential equation, a next matrix layer of flux values, offset by a predetermined amount in z;
      (iii) store the flux values of the next matrix layer determined at step (ii);
      (iv) set the flux values of the initial matrix layer equal to the flux values of the next matrix layer;
      (v) repeat steps (ii) and (iv) until flux values have been determined for the entire volume of interest;
   (c) using the flux values for the entire volume of interest to see if a dose is within a predetermined range;
   (d) control the electron beam directed at the volume of interest according to the incident field $\Psi$ if the dose for the volume of interest is within the range.

2. The method as recited in claim 1 including the additional steps of inputting to the electronic computer a matrix S describing the stopping power of the patient at the elements within the volume of interest and computing the dose D from the matrix layers for the entire volume of interest and the stopping power.

3. The method as recited in claim 1 wherein step (b)(i) approximates the partial differential values as differences between adjacent elements of the $\Psi$ matrix.

4. The method as recited in claim 1 wherein step (b)(i) approximates the partial differential values by means of the Lax-Wendroff method.

5. The method as recited in claim 1 wherein the algebraic approximation of Fermi's partial differential equation provides flux and energy values for each next matrix layer and wherein the flux is stored separately by energy.

6. The method as recited in claim 1 wherein the flux for each next energy layer is assigned an energy determined as a function of z.

7. The method as recited in claim 6 wherein the function of z is derived analytically from Fermi's partial differential equation under the assumption that the patient is homogenous along x and y.

8. The method as recited in claim 1 including the step of acquiring the matrix T by computerized tomography.

9. The method as recited in claim 1 wherein the data of the matrix T is obtained from x-ray attenuation data produced by a computed tomography machine.

* * * * *

UNITED STATES PATENT AND TRADEMARK OFFICE
CERTIFICATE OF CORRECTION

PATENT NO. : 5,418,715
DATED : May 23, 1995
INVENTOR(S) : Joseph O. Deasy

It is certified that error appears in the above-indentified patent and that said Letters Patent is hereby corrected as shown below:

Col. 1, lines 57 and 58  "$\Psi_{\alpha\alpha}$ and $\Psi_{\alpha\alpha}$
should be --$\Psi_{\alpha\alpha}$ and $\Psi_{\beta\beta}$--

Col. 3, line 41  "power matrix $\Psi$"
should be --power matrix T--

Col. 4, line 64  "and $\beta$ where 60"
should be --and $\beta$ where $\alpha$--

All of the following should read
Col. 2, lines 52; 57

Col. 3, lines 26; 29; 42; 44

Col. 4, lines 41; 44; 45; 48; 52; 61

"flux field $\Psi$
should be --flux field $\hat{\Psi}$--

UNITED STATES PATENT AND TRADEMARK OFFICE
CERTIFICATE OF CORRECTION

PATENT NO. : 5,418,715
DATED : May 23, 1995
INVENTOR(S) : Joseph O. Deasy

It is certified that error appears in the above-indentified patent and that said Letters Patent is hereby corrected as shown below:

```
Col. 5, lines 2;    9; 13

Col. 6, lines 6; 8; 10; 63

Col. 8, lines 23; 27; 29

Col. 9; line 51

Col. 10,   lines 15; 20, 21; 36
```

Signed and Sealed this

Twenty-ninth Day of August, 1995

Attest:

BRUCE LEHMAN

*Attesting Officer*  *Commissioner of Patents and Trademarks*